(12) United States Patent
Song (10) Patent No.: US 8,273,535 B2
(45) Date of Patent: Sep. 25, 2012

(54) METHODS FOR DETECTION OF CORN EVENT DAS-59132

(75) Inventor: Ping Song, Carmel, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 215 days.

(21) Appl. No.: 12/864,675

(22) PCT Filed: Feb. 5, 2009

(86) PCT No.: PCT/US2009/033171
§ 371 (c)(1), (2), (4) Date: Jul. 27, 2010

(87) PCT Pub. No.: WO2009/100188
PCT Pub. Date: Aug. 13, 2009

(65) Prior Publication Data
US 2011/0129829 A1 Jun. 2, 2011

Related U.S. Application Data (60) Provisional application No. 61/065,165, filed on Feb. 8, 2008.

(51) Int. Cl.
*C12P 19/34* (2006.01)
*C12Q 1/68* (2006.01)
*C07H 21/04* (2006.01)

(52) U.S. Cl. .................... 435/6.12; 536/24.33; 435/91.2

(58) Field of Classification Search .................. None
See application file for complete search history.

(56) References Cited

FOREIGN PATENT DOCUMENTS

| WO | 03/052073 | 6/2003 |
|---|---|---|
| WO | 03601589 | 7/2003 |
| WO | 2004/099447 | 11/2004 |
| WO | 2005-103266 | 11/2005 |
| WO | 2006039376 | 4/2006 |

OTHER PUBLICATIONS

Form PCT/ISA/210, International Search Report for International application No. PCT/US2009/033171.
Form PCT/ISA/237, Written Opinion of the International Searching Authority (PCT Rule 43bis. 1) for International application No. PCT/US2009/033171.
Gao Yong et al: "Characterization of Cry34Ab1 and Cry35Ab1 insecticidal crystal proteins expressed in transgenic corn plants and *Pseudomonas fluorescens*."; Journal of Agricultural and Food Chemistry, vol. 52, No. 26, Dec. 29, 2004, pp. 8057-8065, XP002528713 ISSN: 0021-8561 table 1.
Mollenbeck Daniel J et al: "Insecticidal proteins from *Bacillus thuringiensis*" Nature Biotechnology, vol. 19, No. 7, Jul. 2001, pp. 668-672, XP002528714 ISSN: 1087-0156 the whole document.
James Delano et al; "Reliable detection and identification of genetically modified maize, soybean, and canola by multiplex PCR analysis" Journal of Agricultural and Food Chemistry, American Chemical Society, Washington, US. vol. 51, No. 20, Sep. 24, 2003, pp. 5829-5834, XP0024333742.

*Primary Examiner* — Samuel Woolwine
*Assistant Examiner* — Suchira Pande
(74) *Attorney, Agent, or Firm* — Ronald S. Maciak; Carl D. Corvin; Donald S. Stuart (57) ABSTRACT

The invention provides assays for detecting the presence of the maize DAS-59132 event based on the DNA sequence of the recombinant construct inserted into the maize genome and the DNA sequences flanking the insertion site. Kits and conditions useful in conducting the assays are provided.

8 Claims, 2 Drawing Sheets

Figure 1

```
  1    CGTGCAAGCG CTCAATTCGC CCTATAGTGA GTCGTATTAC AATCGTACGC
 51    AATTCAGTAC ATTAAAAACG TCCGCAATGT GTTATTAAGT TGTCTAAGCG
101    TCAATTTGTT TACACCAGAG GCCGACACGG CACACACGGC GACATTCACC
151    GCCGGCTTCC TCCGTCGCCA CTCGGCACAA GGCTCATCAG TCGCCGATGC
201    CCGATGCGAT CAACGGAAGC GGATGGCCCG CTTCTTTAGA ATTGGCACAG
251    GAACACTGGC CACTGCCCTT GATGTGCAAT TATGCCTGCG AAAGCCTAGG
301    CAACACACGC GAATAAACGA GCGAATGACA CGGAAAGCTG ATGTGGTATG
351    AATTATACAA CATTATGGGC CAAAATATTA TTCTATCCAC CATTGTGTAG
401    CCACAGCATC GGTATTTGAG TTGTGCGAGG ACAAATCCCT CGTGAGGTCA
451    AAAACAGCAA ATAATAAACC CATCTCCTGA AGACACCAAA AAAAAGGAGC
501    AGCTCCTCGT GTCAATGAAC AAGCGTCACA AGAAAAGGGA GCACGTAAAT
551    AACCTCTTCA ATTGCTTCAG CATGAAAAGA ACGGGAAGAA ATGCAAGTCT
                                                       NcoI
601    ACAGAGGAAA GTGCAGCTGT TTCGGCTGCC ATGGCAAGTT CCTACATGGG
651    CGAGGAAAAG CTGAACTGGA TTCCAGTCTT CGCGCTGTCA TGCTCAGCTT
701    GCTTTAGGAT GCGGCAATAG TTCACCTGGA TGAAAAGAT ACAAGTTAGT
                                                      HindIII
751    CTTGAAGCAG TCGAGTGGAC ATCCAAAGTA TCAAAATCGA AAGCTTGTAA
801    ATGGGGAAGG AAATATACCT CTACCCGGAA AAGTTTGGTA GGCAAATAA
                   SacI
851    TCCCAACGCC AGCAGAGCTC   (Seq. ID No. 3)
```

FIGURE 2

Panel A: PCR amplification of maize alcohol dehydrenase;
Panel B: Event 59132 specific PCR amplification
Primer set 1 was used; PCR condition: 5 min at 98°C, 98°C for 15 sec, 58°C for 30 sec, 72°C for 75 sec for 35 cycles; About 100 ng of genomic DNA was used in each reaction.

Lane Assignment

| Lane | Description |
|---|---|
| 1, 17 | DNA size marker |
| 2 | H2O as negative control |
| 3 | Non transgenic maize 5HX751 |
| 4 | Non transgenic maize 5HX751 |
| 5 | Non-transgenic maize H-2 |
| 6 | Event 59132 |
| 7 | Maize Event 6317 |
| 8 | Maize Event 59110 |
| 9 | Maize Event 6275 |
| 10 | Maize Event 6275 |
| 11 | Non transgenic maize 5HX751 |
| 12 | Maize Event 59110 |
| 13 | Event 59132 |
| 14 | Maize Event 6317 |
| 15 | Tobacco genomic DNA |
| 16 | Transgenic cotton Event 3006-210-23 |

METHODS FOR DETECTION OF CORN EVENT DAS-59132

CROSS REFERENCE TO RELATED APPLICATIONS

This application claims the benefit of U.S. Provisional Patent Application No. 61/065,165, filed Feb. 8, 2008, and International Patent Application No. PCT/US2009/033171, filed Feb. 5, 2009, and are incorporated in their entirety.

FIELD OF INVENTION

The field of the present invention is plant biotechnology. The invention relates to event-specific methods for detecting the presence maize event DAS-59132 in a sample of plant material.

BACKGROUND OF INVENTION

Corn is an important crop and is a primary food source in many areas of the world. Damage caused by insect pests is a major factor in the loss of the world's corn crops, despite the use of protective measures such as chemical pesticides. In view of this, insect resistance has been genetically engineered into crops such as corn in order to control insect damage and to reduce the need for traditional chemical pesticides. One group of genes which have been utilized for the production of transgenic insect resistant crops are the delta-endotoxins from *Bacillus thuringiensis* (B.t.). Delta-endotoxins have been successfully expressed in crop plants such as cotton, potatoes, rice, sunflower, as well as corn, and have proven to provide excellent control over insect pests. (Perlak, F. J et al. (1990) *Bio/Technology* 8, 939-943; Perlak, F. J. et al. (1993) *Plant Mol. Biol.* 22: 313-321; Fujimoto H. et al. (1993) *Bio/Technology* 11: 1151-1155; Tu et al. (2000) *Nature Biotechnology* 18:1101-1104; PCT publication number WO 01/13731; and Bing J W et al. (2000) Efficacy of Cry1F Transgenic Maize, 14*th* Biennial International Plant Resistance to Insects Workshop, Fort Collins, Colo.).

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al., *Ann. Rev. Genet* 22:421-477, 1988). At the same time the presence of the transgene at different locations in the genome will influence the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgene by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in United States Patent Application 2006/0070139 for maize event DAS-59122-7, a sister event to DAS 59132. It would be desirable to have a simple and discriminative method for the identification of event DAS-59132.

SUMMARY OF INVENTION

An embodiment of this invention relates to detection of the transgene/flanking insertion region in corn plant DAS-59132 and progeny thereof.

Maize event DAS-59132 A was produced by Agrobacterium mediated insertion into maize of DNA from a molecule named PHI17662A, which includes three (3) transgene expression cassettes between right and left T-DNA borders. The first expression cassette in PHI17662A comprises a DNA molecule which includes the promoter, 5' untranslated exon, and first intron of the maize ubiquitin (Ubi-1) gene (Christensen et al. (1992) *Plant Mol. Biol.* 18:675-689 and Christensen and Quail (1996) *Transgenic Res.* 5:213-218) operably connected to a DNA molecule encoding a B.t. δ-endotoxin identified as Cry34Ab1 (U.S. Pat. Nos. 6,127,180, 6,624,145 and 6,340,593) operably connected to a DNA molecule comprising a Pin II transcriptional terminator isolated from potato (Gyheung An et al. (1989) *Plant Cell.* 1:115-122). The second transgene expression cassette of the DNA construct comprises a DNA molecule encoding the wheat peroxidase promoter (Hertig et al. (1991) *Plant Mol. Biol.* 16:171-174) operably connected to a DNA molecule encoding a B.t. δ-endotoxin identified as Cry35Ab1 (U.S. Pat. Nos. 6,083,499, 6,548,291 and 6,340,593) operably connected to a DNA molecule comprising a Pin II transcriptional terminator isolated from potato (Gyheung An et al. (1989) *Plant Cell.* 1:115-122). The third transgene expression cassette of the DNA construct comprises a DNA molecule of the cauliflower mosaic virus (CaMV) 35S promoter (Odell J. T. et al. (1985) *Nature* 313: 810-812; Mitsuhara et al. (1996) *Plant Cell Physiol.* 37: 49-59) operably connected to a DNA molecule encoding a phosphinothricin acetyltransferase (PAT) gene (Wohlleben W. et al. (1988) *Gene* 70: 25-37) operably connected to a DNA molecule comprising a 3' transcriptional terminator from (CaMV) 35S (see Mitsuhara et al. (1996) *Plant Cell Physiol*. 37: 49-59).

Certain embodiments of the invention provide, compositions and methods for determining whether a sample of corn plant material contains the 3' transgene/flanking insertion region (3' junction) characteristic of maize event DAS-59132, which methods are based on primers or probes which specifically recognize the 3' flanking sequence of DAS-59132. DNA molecules are provided that comprise primer sequences that when utilized in a PCR reaction will produce amplicons unique to the transgenic event DAS-59132. These molecules may be selected from the group consisting of: SEQ ID NOS: 4, 5, 6, 7, 8, and 9.

Further, kits utilizing these primer sequences for the identification of the DAS-59132 event are provided.

An additional embodiment of the invention relates to the specific 3' flanking sequence of DAS-59132 described herein, which can be used to develop specific identification methods for DAS-59132 in biological samples. More particularly, the invention relates to the 3' flanking regions of DAS-59132, SEQ ID NO: 2, which can be used for the development of specific primers and probes. A further embodiment of the invention relates to identification methods for the presence of DAS-59132 in biological samples based on the use of such specific primers or probes.

According to another embodiment of the invention, methods of detecting the presence of DNA corresponding to the corn event DAS-59132 in a sample are provided. Such methods comprise: (a) contacting the sample comprising DNA with a DNA primer set, that when used in a nucleic acid amplification reaction with genomic DNA extracted from corn event DAS-59132 produces an amplicon that is diagnostic for the 3' junction of corn event DAS-59132; (b) performing a nucleic acid amplification reaction, thereby producing the amplicon; and (c) detecting the amplicon.

DNA molecules that comprise the novel 3' transgene/flanking insertion region, SEQ ID NO: 3, and are homologous or complementary to SEQ ID NO: 3 are an embodiment of this invention.

DNA sequences that comprise a sufficient length of polynucleotides of transgene insert sequence and a sufficient length of polynucleotides of maize genomic and/or flanking sequence from maize plant DAS-59132 of SEQ ID NO: 3 that are useful as primer sequences for the production of an amplicon product diagnostic for maize plant DAS-59132 are embodiments of the invention.

According to another embodiment of the invention, primer pairs that comprise at least 11 or more nucleotides of the transgene portion of the DNA sequence of SEQ ID NO: 3 or SEQ ID NO:1, or complements thereof, and a similar length of 3' flanking maize DNA sequence of SEQ ID NO: 3 or complements thereof, which are useful as DNA primers in DNA amplification methods, are provided. The amplicons produced using these primers are diagnostic for maize event DAS-59132. Therefore, embodiments of the invention also include the amplicons produced by such DNA primers.

More specifically, a pair of DNA molecules comprising a DNA primer set, wherein the DNA molecules are identified as SEQ ID NO: 4 or complements thereof and SEQ ID NO: 5 or complements thereof; SEQ ID NO: 6 or complements thereof and SEQ ID NO: 7 or complements thereof; SEQ ID NO: 8 or complements thereof and SEQ ID NO: 9 or complements thereof are embodiments of the invention.

Further embodiments of the invention include the amplicon comprising the DNA molecules of SEQ ID NO: 10, 11, or 12.

According to another embodiment of the invention, methods of detecting the presence of a DNA molecule corresponding to the DAS-59132 event in a sample, such methods comprising: (a) contacting the sample comprising DNA extracted from a corn plant with a DNA probe, molecule that hybridizes under stringent hybridization conditions with DNA extracted from corn event DAS-59132 and does not hybridize under the stringent hybridization conditions with a control corn plant DNA; (b) subjecting the sample and probe to stringent hybridization conditions; and (c) detecting hybridization of the probe to the DNA. More specifically, a method for detecting the presence of a DNA molecule corresponding to the DAS-59132 event in a sample, such methods, consisting of (a) contacting the sample comprising DNA extracted from a corn plant with a DNA probe molecule that consists of sequences that are unique to the 3' junction sequence of the DAS-59132 event, wherein said DNA probe molecule hybridizes under stringent hybridization conditions with DNA extracted from corn event DAS-59132 and does not hybridize under the stringent hybridization conditions with a control corn plant DNA; (b) subjecting the sample and probe to stringent hybridization conditions; and (c) detecting hybridization of the probe to the DNA.

In addition, a kit and methods for identifying event DAS-59132 in a biological sample which detects a DAS-59132 specific region within SEQ ID NO: 3 are provided.

DNA molecules are provided that comprise the 3' junction sequence of DAS-59132 of SEQ ID NO:3 and complements thereof; wherein a junction sequence spans the junction between heterologous DNA inserted into the genome and the DNA from the corn cell flanking the insertion site, i.e. flanking DNA, and is diagnostic for the DAS-59132 event.

Another embodiment of the invention further relates to a DNA detection kit for identifying maize event DAS-59132 in biological samples. The kit comprises a first primer which specifically recognizes the 3' flanking region of DAS-59132, and a second primer which specifically recognizes a sequence within the foreign DNA of DAS-59132, for use in a PCR identification protocol. A further embodiment of the invention relates to a kit for identifying event DAS-59132 in biological samples, which kit comprises a specific probe having a sequence which corresponds or is complementary to, a sequence having between 80% and 100% sequence identity with a specific region of event DAS-59132. The sequence of the probe corresponds to a specific region comprising part of the 3' flanking region of event DAS-59132.

The methods and kits encompassed by the embodiments of the present invention can be used for different purposes such as, but not limited to the following: to identify event DAS-59132 in plants, plant material or in products such as, but not limited to, food or feed products (fresh or processed) comprising, or derived from plant material; additionally or alternatively, the methods and kits can be used to identify transgenic plant material for purposes of segregation between transgenic and non-transgenic material; additionally or alternatively, the methods and kits can be used to determine the quality of plant material comprising maize event DAS-59132. The kits may also contain the reagents and materials necessary for the performance of the detection method.

The foregoing and other aspects of the invention will become more apparent from the following detailed description and accompanying drawing.

DETAILED DESCRIPTION

Figure 1:
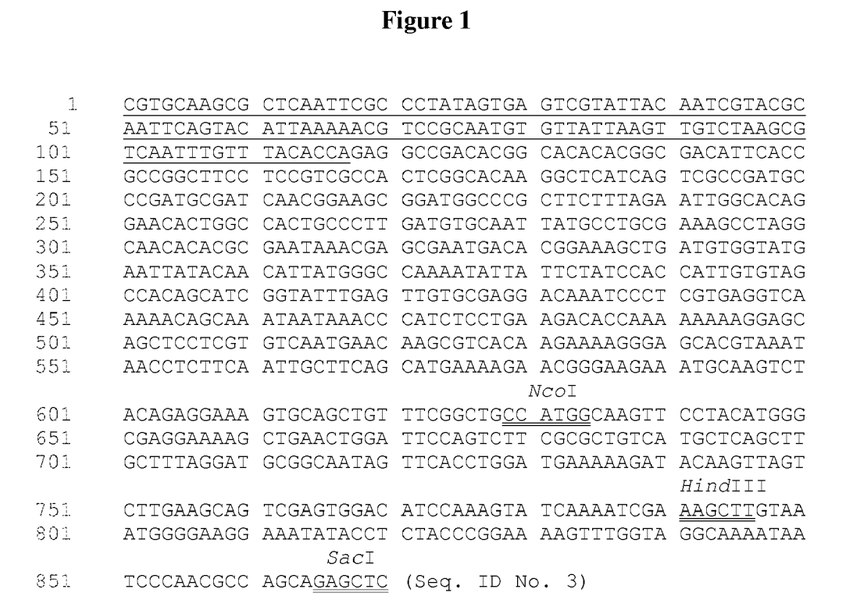
FIG. 1 is the DNA sequence (SEQ ID NO:3) of the 3' junction region of maize event DAS-59132. Underlined sequences are from the T-DNA insert in plasmid PHI17662 that was used to generate the event.
Figure 2:
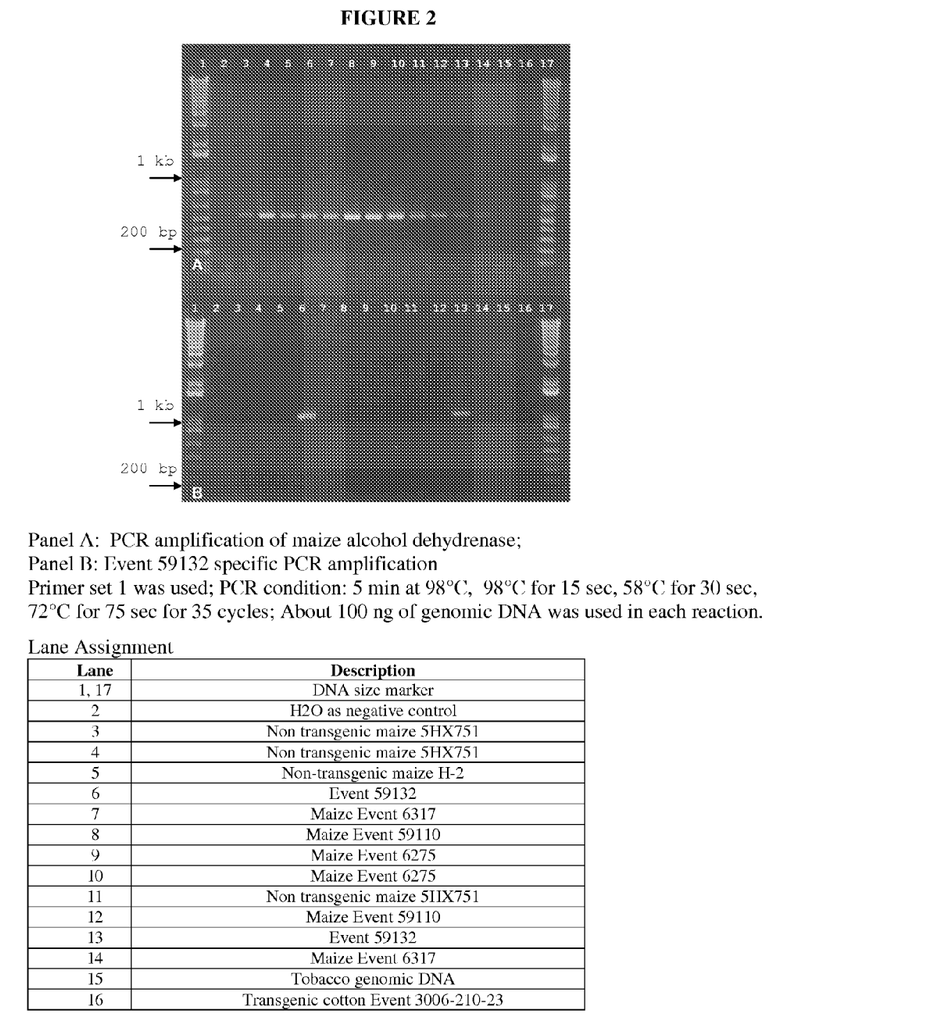
FIG. 2 is a photograph of a gel illustrating event specific PCR detection of DAS-59132.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5$^{th}$ edition, Springer-Verlag; New York, 1991; and Lewin, *Genes V*, Oxford University Press: New York, 1994. The nomenclature for DNA bases as set forth at 37 CFR §1.822 is used.

As used herein, the term "comprising" means "including but not limited to".

As used herein, the term "corn" means *Zea mays* or maize and includes all plant varieties that can be bred with corn, including wild maize species.

As used herein, the term "DAS-59132 specific" refers to a nucleotide sequence which is suitable for discriminatively identifying event DAS-59132 in plants, plant material, or in products such as, but not limited to, food or feed products (fresh or processed) comprising, or derived from plant material.

As used herein, "insert DNA" refers to the heterologous DNA within the expression cassettes used to transform the plant material while "flanking DNA" can exist of either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least twenty (20) base pair, preferably at least fifty (50) base pair, which is located either immediately upstream of and contiguous with or immediately downstream of and contiguous with the original foreign insert DNA molecule. Transformation procedures leading to random integration of the foreign DNA will result in transformants containing different flanking regions characteristic and unique for each transformant. When recombinant DNA is introduced into a plant through traditional crossing, its flanking regions will generally not be changed. Transformants will also contain unique junctions between a piece of heterologous insert DNA and genomic DNA, or two (2) pieces of genomic DNA, or two (2) pieces of heterologous DNA. A "junction" is a point where two (2) specific DNA fragments join. For example, a junction exists where insert DNA joins flanking DNA. A junction point also exists in a transformed organism where two (2) DNA fragments join together in a manner that is modified from that found in the native organism. "Junction DNA" refers to DNA that comprises a junction point.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

A "protein" or "polypeptide" is a chain of amino acids arranged in a specific order determined by the coding sequence in a polynucleotide encoding the polypeptide.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of isolated DNA from corn event DAS-59132 whether from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target nucleic acid sequence, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence specifically in the hybridization conditions or reaction conditions determined by the operator. This length may be of any length that is of sufficient length to be useful in a detection method of choice. Generally, eleven (11) nucleotides or more in length, eighteen (18) nucleotides or more, and twenty-two (22) nucleotides or more, are used. Such probes and primers hybridize specifically to a target sequence under high stringency hybridization conditions. Probes and primers according to embodiments of the present invention may have complete DNA sequence similarity of contiguous nucleotides with the target sequence, although probes differing from the target DNA sequence and that retain the ability to hybridize to target DNA sequences may be designed by conventional methods. Probes can be used as primers, but are generally designed to bind to the target DNA or RNA and are not be used in an amplification process.

Specific primers can be used to amplify an integration fragment to produce an amplicon that can be used as a "specific probe" for identifying event DAS-59132 in biological samples. When the probe is hybridized with the nucleic acids of a biological sample under conditions which allow for the binding of the probe to the sample, this binding can be detected and thus allow for an indication of the presence of event DAS-59132 in the biological sample. Such identification of a bound probe has been described in the art. In an embodiment of the invention the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the event.

Methods for preparing and using probes and primers are described, for example, in *Molecular Cloning: A Laboratory*

Manual, 2nd ed., vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5©, 1991, Whitehead Institute for Biomedical Research, Cambridge, Mass.). Additionally, the sequence can be visually scanned and primers manually identified using guidelines known to one of skill in the art.

A "kit" as used herein refers to a set of reagents for the purpose of performing the method embodiments of the invention, more particularly, the identification of the event DAS-59132 in biological samples. The kit of the invention can be used, and its components can be specifically adjusted, for purposes of quality control (e.g. purity of seed lots), detection of event DAS-59132 in plant material, or material comprising or derived from plant material, such as but not limited to food or feed products. "Plant material" as used herein refers to material which is obtained or derived from a plant.

Primers and probes based on the flanking DNA and insert sequences disclosed herein can be used to confirm (and, if necessary, to correct) the disclosed sequences by conventional methods, e.g., by re-cloning and sequencing such sequences. The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, a Practical Approach*, IRL Press, Washington, D.C. (1985), departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

In hybridization reactions, specificity is typically the function of post-hybridization washes, the critical factors being the ionic strength and temperature of the final wash solution. The thermal melting point (Tm) is the temperature (under defined ionic strength and pH) at which 50% of a complementary target sequence hybridizes to a perfectly matched probe. For DNA-DNA hybrids, the Tm can be approximated from the equation of Meinkoth and Wahl (1984) *Anal. Biochem.* 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm.

Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

As used herein, a substantially homologous sequence is a nucleic acid molecule that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of a destabilizing agent such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. A nucleic acid of the invention may specifically hybridize to one or more of the nucleic acid molecules unique to the DAS-59132 event or complements thereof or fragments of either under moderately stringent conditions.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (version 3.0, copyright 1997); and GAP, BESTFIT, BLAST, FASTA, and TFASTA in the Wisconsin Genetics Software Package, Version 10 (available from Accelrys, 9685 Scranton Road, San Diego, Calif. 92121, USA). Alignments using these programs can be performed using the default parameters.

The CLUSTAL program is well described by Higgins and Sharp, *Gene* 73: 237-244 (1988); Higgins and Sharp, *CABIOS* 5: 151-153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994). The ALIGN and the ALIGN PLUS programs are based on the algorithm of Myers and Miller (1988) supra. The BLAST programs of Altschul et al. (1990) *J. Mol. Biol.* 215:403 are based on the algorithm of Karlin and Altschul (1990) supra. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995). Alignment may also be performed manually by visual inspection.

To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.hlm.nih.gov.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether a corn plant resulting from a sexual cross contains transgenic event genomic DNA from the corn plant of the invention, DNA extracted from the corn plant tissue sample may be subjected to a nucleic acid amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the event DNA. Alternatively, the second primer may be derived from the flanking sequence. The amplicon is of a length and has a sequence that is also diagnostic for the event. The amplicon may range in length from the combined length of the primer pairs plus one nucleotide base pair to any length of amplicon producible by a DNA amplification protocol. A member of a primer pair derived from the flanking sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Nucleic acid amplification can be accomplished by any of the various nucleic acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic press, San Diego, 1990. PCR amplification methods have been developed to amplify up to 22 Kb of genomic DNA and up to 42 Kb of bacteriophage DNA (Cheng et al., *Proc. Natl. Acad. Sci. USA* 91:5695-5699, 1994). These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplicon produced by these methods may be detected by a plurality of techniques, including, but not limited to, Genetic Bit Analysis (Nikiforov, et al. *Nucleic Acid Res.* 22:4167-4175, 1994) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge (*Innov. Pharma. Tech.* 00: 18-24, 2000). In this method an oligonucleotide is designed that overlaps the adjacent DNA and insert DNA junction. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al., (*Genome Res.* 9:492-498, 1999) is also a method that can be used to detect an amplicon of the invention. Using this method an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al. (*Nature Biotech.* 14:303-308, 1996). Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

EXAMPLES

Example 1

Transformation of Maize by *Agrobacterium* Transformation and Regeneration of Transgenic Plants Containing the Cry34Ab1 and Cry35Ab1 (Cry34/35Ab1) Genes A DNA molecule of approximately 7.4 Kb, designated PHI17662A (SEQ ID NO: 24), which includes a first transgene expression cassette comprising a DNA molecule which includes the promoter, 5' untranslated exon, and first intron of the maize ubiquitin (Ubi-1) gene (Christensen et al. (1992) *Plant Mol. Biol.* 18:675-689 and Christensen and Quail (1996) *Transgenic Res.* 5:213-218) operably connected to a DNA molecule encoding a B.t. δ-endotoxin identified as Cry34Ab1 (U.S. Pat. Nos. 6,127,180, 6,624,145 and 6,340,593) operably connected to a DNA molecule comprising a Pin II transcriptional terminator isolated from potato (Gyheung An et al. (1989) *Plant Cell.* 1:115-122). The second transgene expression cassette of the DNA construct comprises a DNA molecule encoding the wheat peroxidase promoter (Hertig et al. (1991) *Plant Mol. Biol.* 16:171-174) operably connected to a DNA molecule encoding a B.t. δ-endotoxin identified as Cry35Ab1 (U.S. Pat. Nos. 6,083,499, 6,548,291 and 6,340,593) operably connected to a DNA molecule comprising a Pin II transcriptional terminator isolated from potato (Gyheung An et al. (1989) *Plant Cell.* 1:115-122). The third transgene expression cassette of the DNA construct comprises a DNA molecule of the cauliflower mosaic virus (CaMV) 35S promoter (Odell J. T. et al. (1985) *Nature* 313: 810-812; Mitsuhara et al. (1996) *Plant Cell Physiol.* 37: 49-59) operably connected to a DNA molecule encoding a phosphinothricin acetyltransferase (PAT) gene (Wohlleben W. et al. (1988) *Gene* 70: 25-37) operably connected to a DNA molecule comprising a 3' transcriptional terminator from (CaMV) 35S (see Mitsuhara et al. (1996) *Plant Cell Physiol.* 37: 49-59) was used to transform maize embryo tissue.

B.t. Cry34/35 Ab1 maize plants were obtained by Agrobacterium transformation, the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of *Agrobacterium*, where the bacteria was capable of transferring PHI17662 DNA (SEQ ID NO:24) to at least one cell of at least one of the immature embryos (step 1: the infection step). Specifically, in this step the immature embryos were immersed in an *Agrobacterium* suspension for the initiation of inoculation. The embryos were co-cultured for a time with the *Agrobacterium* (step 2: the co-cultivation step). Specifically, the immature embryos were cultured on solid medium following the infection step. Following this co-cultivation period a "resting" step was provided. In this resting step, the embryos were incubated in the presence of at least one antibiotic known to inhibit the growth of *Agrobacterium* without the addition of a selective agent for plant transformants (step 3: resting step). In particular, the immature embryos are cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). Specifically, the immature embryos were cultured on solid medium with a selective agent resulting in the selective growth of transformed cells. The callus was then regenerated into plants (step 5: the regeneration step), and, specifically, calli grown on selective medium were cultured on solid medium to regenerate the plants. Individual embryos were kept physically separate during culture, and the majority of explants died on the selective medium.

Those embryos that survived and produced healthy, glufosinate-resistant callus tissue were assigned unique identification codes representing putative transformation events, and continually transferred to fresh selection medium. Plants were regenerated from tissue derived from each unique event and transferred to the greenhouse. Leaf samples were taken for molecular analysis to verify the presence of the transgene by PCR and to confirm expression of the Cry34/35Ab1 protein by ELISA. Plants were then subjected to a whole plant bioassay using western corn rootworm insects. Positive plants were crossed with inbred lines to obtain seed from the initial transformed plants. A number of lines were evaluated in the field. The DAS-59132 event was selected from a population of independent transgenic events based on a superior combination of characteristics, including insect resistance and agronomic performance.

Example 2

T-DNA Insert and Flanking Border Region Sequencing of *Bacillus thuringiensis* Cry34/35Ab1 Maize Line DAS-59132

The sequence bordering the junction at the 3' end of the insert in event DAS-59132 was obtained Primers, shown in Table 1, are designed based on SEQ ID NOS: 1, 2, and 3 to amplify fragments spanning the unique 3' junction of the T-DNA with the corn genomic DNA.

TABLE 1

Primer Sequences

| Primer | Sequence (5'-3') | Target Sequence Location (bp to bp)[1] |
|---|---|---|
| SEQ ID NO: 4 | gcccgctgaaatcaccagtct | bp 6929-6949 of SEQ ID NO: 1 |
| SEQ ID NO: 5 | gtaggaacttgccatggcag (complementary strand) | bp 626-645 of SEQ ID NO: 3 |
| SEQ ID NO: 6 | cgtgcaagcgctcaattcgc | bp 7259-7278 of SEQ ID NO: 1 bp 1-20 in SEQ ID NO: 3 |
| SEQ ID NO: 7 | tccaggtgaactattgccgca (complementary strand) | bp 710-730 of SEQ ID NO: 3 |
| SEQ ID NO: 8 | ccgcaatgtgttattaagttgt ctaag | bp 7330-7356 in SEQ ID NO: 1 |
| SEQ ID NO: 9 | ggtgaatgtcgccgtgtgt | bp 132-150 of SEQ ID NO: 3 |

Amplicons corresponding to the primers described in Table 1 are shown in Table 2.

TABLE 2

PCR Primer and Amplicon Descriptions

| PCR Amplicon | Size (bp) | Target Sequence | Forward Primer | Reverse Primer |
|---|---|---|---|---|
| SEQ ID NO: 10 | 975 | 3' junction | SEQ ID NO: 4 | SEQ ID NO: 5 |
| SEQ ID NO: 11 | 730 | 3' junction | SEQ ID NO: 6 | SEQ ID NO: 7 |
| SEQ ID NO: 12 | 79 | 3' junction | SEQ ID NO: 8 | SEQ ID NO: 9 |

Primers designed to amplify fragments across the junction of the 3' border sequence and T-DNA insert were used to establish event-specific PCR fragments for event DAS-59132. For PCR amplifications, Advantage™-GC 2 PCR kit (BD Biosciences) may be used according to manufacturer's instructions. Approximately 10-100 ng of genomic DNA template is used per 50 μL PCR reaction. PCR conditions are as follows: initial template denaturation at 94° C. for 5 min, followed by 35 cycles of 95° C. for 1 minute, 60° C. for 2 minutes, and 72° C. for 3 min, with final extension at 72° C. for 7 min. The PCR amplification products are visualized under UV light following electrophoresis through a 1% agarose gel with 1×TBE and ethidium bromide.

The 3' end regions of the T-DNA insert was found to be intact, except for deletion of the last 15 bp at the 3' end encompassing the T-DNA Border region. While T-DNA border sequences are known to play a critical role in T-DNA insertion into the genome, this result is not unexpected since insertions are often imperfect.

Example 3

PCR Primers

DNA event specific primer pairs were used to produce an amplicon diagnostic for DAS-59132. These event primer pairs include, but are not limited to, In addition to these primer pairs, any primer pair derived from SEQ ID NOS: 1, 2, and 3 that when used in a DNA amplification reaction produces a DNA amplicon diagnostic for DAS-59132 is an embodiment of the present invention. Any modification of these methods that use DNA primers or complements thereof to produce an amplicon DNA molecule diagnostic for DAS-59132 is within the ordinary skill of the art. The analysis of plant tissue DNA extracts to test for the presence of the DAS-59132 event should include a positive tissue DNA extract control (a DNA sample known to contain the transgenic sequences). A successful amplification of the positive control demonstrates that the PCR was run under conditions that allow for the amplification of target sequences. A negative, or wild-type, DNA extract control in which the template DNA provided is either genomic DNA prepared from a non-transgenic plant, or is a non-DAS-59132 transgenic plant, should also be included. Additionally a negative control that contains no template corn DNA extract will be a useful gauge of the reagents and conditions used in the PCR protocol.

Additional DNA primer molecules of sufficient length can be selected from SEQ ID NOS: 1, 2, and 3 by those skilled in the art of DNA amplification methods, and conditions optimized for the production of an amplicon diagnostic for event DAS-59132. The use of these DNA primer sequences with modifications to the methods shown in these Examples are within the scope of the invention. The amplicon wherein at least one DNA primer molecule of sufficient length derived from SEQ ID NO: 2 that is diagnostic for event DAS-59132 is an embodiment of the invention. The amplicon wherein at least one DNA primer of sufficient length derived from SEQ ID NO: 1 is an embodiment of the invention. The assay for the DAS-59132 amplicon can be performed by using a Stratagene Robocycler, MJ Engine, Perkin-Elmer 9700, or Eppendorf Mastercycler Gradient thermocycler, or by methods and apparatus known to those skilled in the art.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A method for identifying event DAS-59132 in a biological sample, comprising detecting the 3' junction of DAS-59132 with a probe or first primer which specifically recognizes a sequence within SEQ ID NO: 2.

2. The method of claim 1, further comprising amplifying a DNA fragment from a nucleic acid present in said biological sample using a polymerase chain reaction with at least two primers, wherein said first primer recognizes a sequence within SEQ ID NO: 2, and a second primer recognizes a sequence within bp 1-117 of SEQ ID NO:3.

3. The method of claim 2 wherein said first and second primers comprise SEQ ID NO:4 and SEQ ID NO:5, or SEQ ID NO:6 and SEQ ID NO:7, or SEQ ID NO:8 and SEQ ID NO:9.

4. A kit for identifying event DAS-59132 in a biological sample which detects a DAS-59132 specific 3' junction region, said kit comprising at least a first primer, which recognizes a sequence within SEQ ID NO: 2.

5. The kit of claim 4 further comprising at least a second primer which recognizes a sequence within bp 1-117 of SEQ ID NO:3.

6. The kit of claim 5, wherein said at least first and second primers comprise the sequence of SEQ ID NO:4 and SEQ ID NO:5, respectively.

7. The kit of claim 5, wherein said at least first and second primers comprise the sequence of SEQ ID NO:6 and SEQ ID NO:7, respectively.

8. The kit of claim 5, wherein said at least first and second primers comprise the sequence of SEQ ID NO:8 and SEQ ID NO:9, respectively.

* * * * *

SEQUENCE LISTING

```
<160> NUMBER OF SEQ ID NOS: 12

<210> SEQ ID NO 1
<211> LENGTH: 7390
<212> TYPE: DNA
<213> ORGANISM: Artificial
<220> FEATURE:
<223> OTHER INFORMATION: This seqeunce represents the DNA molecule used
      to transform maize line DAS-51932 and represents insert PHI17622A

<400> SEQUENCE: 1
gtttacccgc caatatatcc tgtcaaacac tgatagttta aactgaaggc gggaaacgac        60
aatctgatca tgagcggaga attaagggag tcacgttatg accccgccg atgacgcggg       120 acaagccgtt ttacgtttgg aactgacaga accgcaacgt tgaaggagcc actcagcaag       180
cttactagta gcgctgttta aacgctcttc aactggaaga gcggttaccc ggaccgaagc       240
ttgcatgcct gcagtgcagc gtgacccggt cgtgcccctc tctagagata atgagcattg       300
catgtctaag ttataaaaaa ttaccacata tttttttgt cacacttgtt tgaagtgcag       360
tttatctatc tttatacata tatttaaact ttactctacg aataatataa tctatagtac       420
tacaataata tcagtgtttt agagaatcat ataaatgaac agttagacat ggtctaaagg       480
acaattgagt attttgacaa caggactcta cagttttatc tttttagtgt gcatgtgttc       540
tccttttttt ttgcaaatag cttcacctat ataatacttc atccatttta ttagtacatc       600
catttagggt ttagggttaa tggtttttat agactaattt ttttagtaca tctattttat       660
tctattttag cctctaaatt aagaaaacta aaactctatt ttagttttt tatttaataa       720 tttagatata aaatagaata aaataaagtg actaaaaatt aaacaaatac cctttaagaa       780
attaaaaaaa ctaaggaaac attttttcttg tttcgagtag ataatgccag cctgttaaac       840
```

-continued

```
gccgtcgacg agtctaacgg acaccaacca gcgaaccagc agcgtcgcgt cgggccaagc      900
gaagcagacg gcacggcatc tctgtcgctg cctctggacc cctctcgaga gttccgctcc      960
accgttggac ttgctccgct gtcggcatcc agaaattgcg tggcggagcg cagacgtga      1020
gccggcacgg caggcggcct cctcctcctc tcacggcacc ggcagctacg ggggattcct     1080
ttcccaccgc tccttcgctt tcccttcctc gcccgccgta ataaatagac accccctcca     1140
caccctcttt ccccaacctc gtgttgttcg gagcgcacac acacacaacc agatctcccc     1200
caaatccacc cgtcggcacc tccgcttcaa ggtacgccgc tcgtcctccc cccccccccc     1260
tctctacctt ctctagatcg gcgttccggt ccatggttag ggcccggtag ttctacttct     1320
gttcatgttt gtgttagatc cgtgtttgtg ttagatccgt gctgctagcg ttcgtacacg     1380
gatgcgacct gtacgtcaga cacgttctga ttgctaactt gccagtgttt ctctttgggg     1440
aatcctggga tggctctagc cgttccgcag acgggatcga tttcatgatt ttttttgttt     1500
cgttgcatag ggtttggttt gcccttttcc tttatttcaa tatatgccgt gcacttgttt     1560
gtcgggtcat cttttcatgc ttttttttgt cttggttgtg atgatgtggt ctggttgggc     1620
ggtcgttcta gatcggagta gaattctgtt tcaaactacc tggtggattt attaattttg     1680
gatctgtatg tgtgtgccat acatattcat agttacgaat tgaagatgat ggatggaaat     1740
atcgatctag gataggtata catgttgatg cgggttttac tgatgcatat acagagatgc     1800
ttttttgttcg cttggttgtg atgatgtggt gtggttgggc ggtcgttcat tcgttctaga     1860
tcggagtaga atactgtttc aaactacctg gtgtatttat taattttgga actgtatgtg     1920
tgtgtcatac atcttcatag ttacgagttt aagatggatg gaaatatcga tgtaggatag     1980
gtatacatgt tgatgtgggt tttactgatg catatacatg atggcatatg cagcatctat     2040
tcatatgctc taaccttgag tacctatcta ttataataaa caagtatgtt ttataattat     2100
tttgatcttg atatacttgg atgatggcat atgcagcagc tatatgtgga tttttttagc     2160
cctgccttca tacgctattt atttgcttgg tactgtttct tttgtcgatg ctcaccctgt     2220
tgtttggtgt tacttctgca ggtcgactct agaggatcca cacgacacca tgtccgcccg     2280
cgaggtgcac atcgacgtga acaacaagac cggcccacac ctccagctgg aggacaagac     2340
caagctcgac ggcggcaggt ggcgcacctc cccgaccaac gtggccaacg accagatcaa     2400
gaccttcgtg gccgaatcca acggcttcat gaccggcacc gagggcacca tctactactc     2460
aattaatggc gaggccgaga tcagcctcta cttcgacaac ccgttcgccg gctccaacaa     2520
atacgacggc cactccaaca gtcccagta cgagatcatc acccagggcg gctccggcaa     2580
ccagtcccac gtgacctaca ccatccagac cacctcctcc cgctacggcc acaagtcctg     2640
agtcatgagt catgagtcag ttaacctaga cttgtccatc ttctggattg gccaacttaa     2700
ttaatgtatg aaataaaagg atgcacacat agtgacatgc taatcactat aatgtgggca     2760
tcaaagttgt gtgttatgtg taattactag ttatctgaat aaaagagaaa gagatcatcc     2820
atatttctta tcctaaatga atgtcacgtg tctttataat tctttgatga accagatgca     2880
tttcattaac caaatccata tacatataaa tattaatcat atataattaa tatcaattgg     2940
gttagcaaaa caaatctagt ctaggtgtgt tttgcgaatg cggccgcgga ccgaattggg     3000
gatctgcatg aaagaaactg tcgcactgct gaaccgcacc ttgtcacttt catcgaacac     3060
gacctgtgcc caagatgacg gtgctgcggt ctaagtgagg ctgaattgcc ttggacagaa     3120
gcggactccc tacaattagt taggccaaac ggtgcatcca tgtgtagctc cgggctcggg     3180
ctgtatcgcc atctgcaata gcatccatgg agctcgttcc atgtagttgg agatgaacca     3240
```

```
atgatcgggc gtgtggacgt atgttcctgt gtactccgat agtagagtac gtgttagctc   3300
tttcatggtg caagtgaaat ttgtgttggt ttaattaccc ctacgttagt tgcgggacag   3360
gagacacatc atgaatttaa aggcgatgat gtcctctcct gtaatgttat tcttttgatg   3420
tgatgaatca aaatgtcata taaaacattt gttgctcttt agttaggcct gatcgtagaa   3480
cgaaatgctc gtgtagcggg gctacgagcc tatgacgcaa taacactggt ttgccggccc   3540
ggagtcgctt gacaaaaaaa agcatgttaa gtttatttac aattcaaaac ctaacatatt   3600
atattccctc aaagcaggtt cacgatcaca cctgtaccta aaaaaaacat gaagaatata   3660
ttactccatt attatgagat gaaccacttg gcaagagtgg taagctatat aaaaaaatga   3720
acattattac gagatgttat atgccattat attgattcga agatatatgt ttctttctcc   3780
cacgggcacc taacggatac atgataaggc caaggcagat cacgggaaat tattcgaata   3840
catgttacgc cctattgccg aaaaaaaaat gcagggcagg tgttggccgt agcgatttaa   3900
gcacttaagc tggaggttgc cacacttgga tgcaagcgtc tgacccttct aaaaaatcgg   3960
cggctttgtc cgtatccgta tccctatcc aacatctagc tggccacacg acggggctgg   4020
gcagatcgtg gatgccgggt cgacgtcgat cgtcagccat catagaccaa tcgaccatct   4080
gttatggatg cttgctagct agactagtca gacataaaat ttggatactt tctcccaact   4140
gggagacggg gactgatgtg cagctgcacg tgagctaaat ttttccctat aaatatgcat   4200
gaaatactgc attatcttgc cacagccact gccacagcca gataacaagt gcagctggta   4260
gcacgcaacg catagctctg gacttgtagc taggtagcca accggatcca cacgacacca   4320
tgctcgacac caacaaggtg tacgagatca gcaaccacgc caacggcctc tacgccgcca   4380
cctacctctc cctcgacgac tccggcgtgt ccctcatgaa caagaacgac gacgacatcg   4440
acgactacaa cctcaagtgg ttcctcttcc cgatcgacga cgaccagtac atcatcacct   4500
cctacgccgc caacaactgc aaggtgtgga acgtgaacaa cgacaagatt aatgtgtcaa   4560
cctactcctc caccaactcc atccagaagt ggcagatcaa ggccaacggc tcctcctacg   4620
tgatccagtc cgacaacggc aaggtgctca ccgccggcac cggccaggcc ctcggcctca   4680
tccgcctcac cgacgagtcc tccaacaacc cgaaccagca atggaacctg acgtccgtgc   4740
agaccatcca gctcccgcag aagccgatca tcgacaccaa gctcaaggac tacccgaagt   4800
actccccgac cggcaacatc gacaacggca cctcccccgca gctcatgggc tggaccctcg   4860
tgccgtgcat catggtgaac gacccgaaca tcgacaagaa cacccagatc aagaccaccc   4920
cgtactacat cctcaagaag taccagtact ggcagagggc cgtgggctcc aacgtcgcgc   4980
tccgcccgca cgagaagaag tcctacacct acgagtgggg caccgagatc gaccagaaga   5040
ccaccatcat caacacccctc ggcttccaga tcaacatcga cagcggcatg aagttcgaca   5100
tcccggaggt gggcggcggt accgacgaga tcaagaccca gctcaacgag gagctcaaga   5160
tcgagtattc acatgagacg aagatcatgg agaagtacca ggagcagtcc gagatcgaca   5220
acccgaccga ccagtccatg aactccatcg gcttcctcac catcacctcc ctggagctct   5280
accgctacaa cggctccgag atccgcatca tgcagatcca gacctccgac aacgacacct   5340
acaacgtgac ctcctacccg aaccaccagc aggccctgct gctgctgacc aaccactcct   5400
acgaggaggt ggaggagatc accaacatcc cgaagtccac cctcaagaag ctcaagaagt   5460
actacttctg agtcatgagt catgagtcag ttaacctaga cttgtccatc ttctggattg   5520
gccaacttaa ttaatgtatg aaataaaagg atgcacacat agtgacatgc taatcactat   5580
aatgtgggca tcaaagttgt gtgttatgtg taattactag ttatctgaat aaaagagaaa   5640
```

```
gagatcatcc atatttctta tcctaaatga atgtcacgtg tctttataat tctttgatga    5700
accagatgca tttcattaac caaatccata tacatataaa tattaatcat atataattaa    5760
tatcaattgg gttagcaaaa caaatctagt ctaggtgtgt tttgcgaatt cccatggagt    5820
caaagattca aatagaggac ctaacagaac tcgccgtaaa gactggcgaa cagttcatac    5880
agagtctctt acgactcaat gacaagaaga aaatcttcgt caacatggtg gagcacgaca    5940
cgcttgtcta ctccaaaaat atcaaagata cagtctcaga agaccaaagg gcaattgaga    6000
cttttcaaca aagggtaata tccggaaacc tcctcggatt ccattgccca gctatctgtc    6060
actttattgt gaagatagtg gaaaggaag gtggctccta caaatgccat cattgcgata    6120
aaggaaaggc catcgttgaa gatgcctctg ccgacagtgg tcccaaagat ggaccccac    6180 ccacgaggag catcgtggaa aaagaagacg ttcaaccac gtcttcaaag caagtggatt    6240
gatgtgatat ctccactgac gtaagggatg acgcacaatc ccactatcct tcgcaagacc    6300
cttcctctat ataaggaagt tcatttcatt tggagaggac agggtacccg gggatccacc    6360
atgtctccgg agaggagacc agttgagatt aggccagcta cagcagctga tatggccgcg    6420
gtttgtgata tcgttaacca ttacattgag acgtctacag tgaactttag gacagagcca    6480
caaacaccac aagagtggat tgatgatcta gagaggttgc aagatagata cccttggttg    6540
gttgctgagg ttgagggtgt tgtggctggt attgcttacg ctgggccctg gaaggctagg    6600
aacgcttacg attggacagt tgagagtact gtttacgtgt cacataggca tcaaaggttg    6660
ggcctaggat ccacattgta cacacatttg cttaagtcta tggaggcgca aggttttaag    6720
tctgtggttg ctgttatagg ccttccaaac gatccatctg ttaggttgca tgaggctttg    6780
ggatacacag cccggggtac attgcgcgca gctggataca agcatggtgg atggcatgat    6840
gttggttttt ggcaaaggga ttttgagttg ccagctcctc caaggccagt taggccagtt    6900
acccagatct gagtcgacct gcaggcatgc ccgctgaaat caccagtctc tctctacaaa    6960
tctatctctc tctataataa tgtgtgagta gttcccagat aagggaatta gggttcttat    7020 aggtttcgc tcatgtgttg agcatataag aaaccttag tatgtatttg tatttgtaaa    7080
atacttctat caataaaatt tctaattcct aaaaccaaaa tccagggcga gctcggtacc    7140
cggggatcct ctagagtcga cctgcaggca tgcccgcgga tatcgatggg ccccggccga    7200
agcttcggtc cgggccatcg tggcctcttg ctcttcagga tgaagagcta tgtttaaacg    7260
tgcaagcgct caattcgccc tatagtgagt cgtattacaa tcgtacgcaa ttcagtacat    7320
taaaaacgtc cgcaatgtgt tattaagttg tctaagcgtc aatttgttta caccacaata    7380
tatcctgcca                                                           7390
```

```
<210> SEQ ID NO 2
<211> LENGTH: 753
<212> TYPE: DNA
<213> ORGANISM: Zea mays

<400> SEQUENCE: 2
gaggccgaca cggcacacac ggcgacattc accgccggct tcctccgtcg ccactcggca      60
caaggctcat cagtcgccga tgcccgatgc gatcaacgga agcggatggc ccgcttcttt     120
agaattggca caggaacact ggccactgcc cttgatgtgc aattatgcct gcgaaagcct     180
aggcaacaca cgcgaataaa cgagcgaatg acacggaaag ctgatgtggt atgaattata     240
caacattatg ggccaaaata ttattctatc caccattgtg tagccacagc atcggtattt     300
gagttgtgcg aggacaaatc cctcgtgagg tcaaaaacag caaataataa acccatctcc     360
```

```
tgaagacacc aaaaaaaagg agcagctcct cgtgtcaatg aacaagcgtc acaagaaaag    420
ggagcacgta ataacctct tcaattgctt cagcatgaaa agaacgggaa gaaatgcaag    480
tctacagagg aaagtgcagc tgtttcggct gccatggcaa gttcctacat gggcgaggaa    540
aagctgaact ggattccagt cttcgcgctg tcatgctcag cttgctttag gatgcggcaa    600
tagttcacct ggatgaaaaa gatacaagtt agtcttgaag cagtcgagtg gacatccaaa    660
gtatcaaaat cgaaagcttg taaatgggga aggaaatata cctctacccg gaaaagtttg    720
gtaggcaaaa taatcccaac gccagcagag ctc                                 753

<210> SEQ ID NO 3
<211> LENGTH: 870
<212> TYPE: DNA
<213> ORGANISM: Artificial
<220> FEATURE:
<223> OTHER INFORMATION: Sequence that represents part of the PHI17662A
      insert as well as flanking sequence 3' to the insert
<220> FEATURE:
<221> NAME/KEY: misc_feature
<222> LOCATION: (117)..(118)
<223> OTHER INFORMATION: Residues 117/118 represent the junction between
      the insert sequence and the flanking sequence. Residue 117 is last
      residue of insert sequence and residue 118 is first residue of
      flanking sequence.
<220> FEATURE:
<221> NAME/KEY: misc_feature
<222> LOCATION: (120)..(121)
<223> OTHER INFORMATION: residue 120 is last residue of insert and
      residue 121 is first residue of flanking region

<400> SEQUENCE: 3
cgtgcaagcg ctcaattcgc cctatagtga gtcgtattac aatcgtacgc aattcagtac     60
attaaaaacg tccgcaatgt gttattaagt tgtctaagcg tcaatttgtt tacaccagag    120
gccgacacgg cacacacggc gacattcacc gccggcttcc tccgtcgcca ctcggcacaa    180
ggctcatcag tcgccgatgc ccgatgcgat caacggaagc ggatggcccg cttctttaga    240
attggcacag gaacactggc cactgccctt gatgtgcaat tatgcctgcg aaagcctagg    300
caacacacgc gaataaacga gcgaatgaca cggaaagctg atgtggtatg aattatacaa    360
cattatgggc caaaatatta ttctatccac cattgtgtag ccacagcatc ggtatttgag    420
ttgtgcgagg acaaatccct cgtgaggtca aaaacagcaa ataataaacc catctcctga    480
agacaccaaa aaaaggagc agctcctcgt gtcaatgaac aagcgtcaca agaaaggga     540 gcacgtaaat aacctcttca attgcttcag catgaaaaga acgggaagaa atgcaagtct    600
acagaggaaa gtgcagctgt ttcggctgcc atggcaagtt cctacatggg cgaggaaaag    660
ctgaactgga ttccagtctt cgcgctgtca tgctcagctt gctttaggat gcggcaatag    720
ttcacctgga tgaaaagat acaagttagt cttgaagcag tcgagtggac atccaaagta    780
tcaaaatcga agcttgtaa atggggaagg aaatatacct ctacccggaa aagtttggta    840
ggcaaaataa tcccaacgcc agcagagctc                                     870

<210> SEQ ID NO 4
<211> LENGTH: 21
<212> TYPE: DNA
<213> ORGANISM: Artificial
<220> FEATURE:
<223> OTHER INFORMATION: primer in insert bp 6929-6949 of SEQ ID NO:1

<400> SEQUENCE: 4
gcccgctgaa atcaccagtc t                                               21
```

<210> SEQ ID NO 5
<211> LENGTH: 20
<212> TYPE: DNA
<213> ORGANISM: Artificial
<220> FEATURE:
<223> OTHER INFORMATION: primer in flanking region bp 626-645 of
      SEQ ID NO:3

<400> SEQUENCE: 5
gtaggaactt gccatggcag                                               20

<210> SEQ ID NO 6
<211> LENGTH: 20
<212> TYPE: DNA
<213> ORGANISM: Artificial
<220> FEATURE:
<223> OTHER INFORMATION: primer in insert bp 7259-7278 of SEQ ID NO:1

<400> SEQUENCE: 6
cgtgcaagcg ctcaattcgc                                               20

<210> SEQ ID NO 7
<211> LENGTH: 21
<212> TYPE: DNA
<213> ORGANISM: Artificial
<220> FEATURE:
<223> OTHER INFORMATION: primer in 3' flanking region  bp 710-730 of
      SEQ ID NO:3

<400> SEQUENCE: 7
tccaggtgaa ctattgccgc a                                             21

<210> SEQ ID NO 8
<211> LENGTH: 27
<212> TYPE: DNA
<213> ORGANISM: Artificial
<220> FEATURE:
<223> OTHER INFORMATION: primer in insert bp 7330-7356 in SEQ ID NO:1

<400> SEQUENCE: 8
ccgcaatgtg ttattaagtt gtctaag                                       27

<210> SEQ ID NO 9
<211> LENGTH: 19
<212> TYPE: DNA
<213> ORGANISM: Artificial
<220> FEATURE:
<223> OTHER INFORMATION: primer in 3' flanking region bp 132-150 of
      SEQ ID NO:3

<400> SEQUENCE: 9
ggtgaatgtc gccgtgtgt                                                19

<210> SEQ ID NO 10
<211> LENGTH: 975
<212> TYPE: DNA
<213> ORGANISM: Artificial
<220> FEATURE:
<223> OTHER INFORMATION: amplicon using primers of SEQ ID NOS: 4 and 5

<400> SEQUENCE: 10
gcccgctgaa atcaccagtc tctctctaca aatctatctc tctctataat aatgtgtgag    60
tagttcccag ataagggaat tagggttctt atagggtttc gctcatgtgt tgagcatata   120 agaaacccctt agtatgtatt tgtatttgta aaatacttct atcaataaaa tttctaattc  180
ctaaaaccaa aatccagggc gagctcggta cccggggatc tctagagtc gacctgcagg   240

```
catgcccgcg gatatcgatg ggccccggcc gaagcttcgg tccgggccat cgtggcctct    300
tgctcttcag gatgaagagc tatgtttaaa cgtgcaagcg ctcaattcgc cctatagtga    360
gtcgtattac aatcgtacgc aattcagtac attaaaaacg tccgcaatgt gttattaagt    420
tgtctaagcg tcaatttgtt tacaccagag gccgacacgg cacacacggc gacattcacc    480
gccggcttcc tccgtcgcca ctcggcacaa ggctcatcag tcgccgatgc ccgatgcgat    540
caacggaagc ggatggcccg cttctttaga attggcacag gaacactggc cactgccctt    600
gatgtgcaat tatgcctgcg aaagcctagg caacacacgc gaataaacga gcgaatgaca    660
cggaaagctg atgtggtatg aattatacaa cattatgggc caaaatatta ttctatccac    720
cattgtgtag ccacagcatc ggtatttgag ttgtgcgagg acaaatccct cgtgaggtca    780
aaaacagcaa ataataaacc catctcctga agacaccaaa aaaaggagc agctcctcgt     840 gtcaatgaac aagcgtcaca agaaaaggga gcacgtaaat aacctcttca attgcttcag    900
catgaaaaga acgggaagaa atgcaagtct acagaggaaa gtgcagctgt ttcggctgcc    960
atggcaagtt cctac                                                    975
```

```
<210> SEQ ID NO 11
<211> LENGTH: 730
<212> TYPE: DNA
<213> ORGANISM: Artificial
<220> FEATURE:
<223> OTHER INFORMATION: amplicon using primers of SEQ ID NOS: 6 and 7

<400> SEQUENCE: 11
cgtgcaagcg ctcaattcgc cctatagtga gtcgtattac aatcgtacgc aattcagtac     60
attaaaaacg tccgcaatgt gttattaagt tgtctaagcg tcaatttgtt tacaccagag    120
gccgacacgg cacacacggc gacattcacc gccggcttcc tccgtcgcca ctcggcacaa    180
ggctcatcag tcgccgatgc ccgatgcgat caacggaagc ggatggcccg cttctttaga    240
attggcacag gaacactggc cactgccctt gatgtgcaat tatgcctgcg aaagcctagg    300
caacacacgc gaataaacga gcgaatgaca cggaaagctg atgtggtatg aattatacaa    360
cattatgggc caaaatatta ttctatccac cattgtgtag ccacagcatc ggtatttgag    420
ttgtgcgagg acaaatccct cgtgaggtca aaaacagcaa ataataaacc catctcctga    480
agacaccaaa aaaaggagc agctcctcgt gtcaatgaac aagcgtcaca agaaaaggga    540
gcacgtaaat aacctcttca attgcttcag catgaaaaga acgggaagaa atgcaagtct    600
acagaggaaa gtgcagctgt ttcggctgcc atggcaagtt cctacatggg cgaggaaaag    660
ctgaactgga ttccagtctt cgcgctgtca tgctcagctt gctttaggat gcggcaatag    720
ttcacctgga                                                          730
```

```
<210> SEQ ID NO 12
<211> LENGTH: 79
<212> TYPE: DNA
<213> ORGANISM: Artificial
<220> FEATURE:
<223> OTHER INFORMATION: amplicon using primers of SEQ ID NOS:8 and 9

<400> SEQUENCE: 12
ccgcaatgtg ttattaagtt gtctaagcgt caatttgttt acaccagagg ccgacacggc     60
acacacggcg acattcacc                                                 79
```